United States Patent
Santos et al.

(10) Patent No.: US 12,057,230 B2
(45) Date of Patent: Aug. 6, 2024

(54) METHODS AND SYSTEMS FOR DEFINING CLINICAL PATHWAY DEVIATION RULES

(71) Applicant: KONINKLIJKE PHILIPS N.V., Eindhoven (NL)

(72) Inventors: Ricardo da Silva Santos, São Paulo (BR); Carsten Oliver Schirra, Amsterdam (NL); Marcelo Santos, Lagoa Santa (BR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 445 days.

(21) Appl. No.: 16/907,791

(22) Filed: Jun. 22, 2020

(65) Prior Publication Data
US 2021/0012898 A1   Jan. 14, 2021

Related U.S. Application Data

(60) Provisional application No. 62/871,773, filed on Jul. 9, 2019.

(51) Int. Cl.
*G16H 70/20* (2018.01)
*G06F 16/23* (2019.01)
(Continued)

(52) U.S. Cl.
CPC ......... *G16H 50/20* (2018.01); *G06F 16/2379* (2019.01); *G16H 10/60* (2018.01);
(Continued)

(58) Field of Classification Search
CPC ........ G16H 50/20; G16H 40/20; G16H 10/60; G16H 15/00; G16H 20/00; G16H 70/20;
(Continued)

(56) References Cited

U.S. PATENT DOCUMENTS

2012/0117099 A1* 5/2012 Gross .................... G06F 16/215
707/758
2014/0088988 A1* 3/2014 Fairbrothers .......... G16H 10/60
705/2

(Continued)

FOREIGN PATENT DOCUMENTS

WO      2018138601 A1    8/2018

OTHER PUBLICATIONS

Alexandrou et al. "A Holistic Environment for the Design and Execution of Self-Adaptive Clinical Pathways". https://ieeexplore.ieee.org/abstract/document/5585762 (Year: 2010).*

(Continued)

*Primary Examiner* — Alaaeldin M Elshaer

(57) ABSTRACT

A method for alerting a user of a clinical pathways management system to a clinical pathway deviation, comprising: (i) providing a reference ontology comprising information about a plurality of clinical pathways; (ii) defining a domain ontology; (iii) converting the domain ontology to one or more graphical representations of clinical pathways; (iv) generating one or more deviation rules for the clinical pathways; (v) receiving information about one or more interventions relative to a patient being treated using a first clinical pathway; (vi) identifying, by comparing the received information about one or more interventions with the one or more deviation rules for the first clinical pathway, one or more deviations from the first clinical pathway; and (vii) alerting the user of the clinical pathways management system to the identified one or more deviations from the first clinical pathway.

16 Claims, 14 Drawing Sheets

(51) Int. Cl.
  G16H 10/60    (2018.01)
  G16H 15/00    (2018.01)
  G16H 20/00    (2018.01)
  G16H 40/20    (2018.01)
  G16H 50/20    (2018.01)
(52) U.S. Cl.
  CPC ............ G16H 15/00 (2018.01); G16H 20/00 (2018.01); G16H 40/20 (2018.01); G16H 70/20 (2018.01)
(58) Field of Classification Search
  CPC ........... G06F 16/2379; G06F 16/90332; G06F 19/00; G06F 16/901; G06Q 10/06; G06Q 50/22; H04L 29/08
  USPC .......................................................... 705/2, 3
  See application file for complete search history.

(56) References Cited

U.S. PATENT DOCUMENTS

| | | | | |
|---|---|---|---|---|
| 2015/0238692 A1* | 8/2015 | Peterson | ................. | A61N 1/046 604/503 |
| 2018/0181712 A1* | 6/2018 | Ensey | .................... | G16H 40/63 |
| 2021/0407694 A1* | 12/2021 | Deckert | ................. | G16H 15/00 |

OTHER PUBLICATIONS

Fudholi et al. "An Ontology Model for Clinical Pathway Audit", https://ieeexplore.ieee.org/abstract/document/8528615 (Year: 2018).*
Ye et al. ("A Semantics-Based Clinical Pathway Workflow and Variance Management Framework"—(Year: 2008).*
Gonzalez-Ferrer et al. ("Automated generation of patient-tailored electronic care pathways by translating computer-interpretable guidelines into hierarchical task networks" file:///C:/Users/aelshaer/Downloads/1-s2.0-S0933365712001212-main%20(1).pdf(Year: 2013).*
Rojas, E. et al., "Process mining in healthcare: A literature review". Journal of Biomedical Informatics 61 (2016) 224-236.
Ye, Y. et al., "An ontology-based hierarchical semantic modeling approach to clinical pathway workflows". Computers in Biology and Medicine 39 (2009) 722-732.
Kinsman, L. et al., "What is a clinical pathway? Development of a definition to inform the debate". BMC Med. 2010;8(1):31.
Kinsman, L. "Clinical pathway compliance and quality improvement." Nursing Standard. Abstract.
Laguna-Perez, A. et al., "Clinical pathway intervention compliance and effectiveness when used in the treatment of patients with severe sepsis and septic shock at an Intensive Care Unit in Spain." Rev. Latino-Am. Enfermagem. 2012;20(4):635-643.

* cited by examiner

| Clinical pathway concepts | BPMN elements |
|---|---|
| Clinical pathway | Process |
| Care phase | Sub-process |
| Intervention/order | Task |
| Fulfilled by role | Role |
| Intervention/order description | Data input |
| Actions corresponding to intervention/order | Data output/task completion attributes |
| Clinical data gathered during intervention | Data output |
| Intervention dependency | Sequence flow |
| Long-term order | Loop tasks |
| Pathway complete | End event |
| Pathway terminate | Terminate event |
| Condition-based choice | Gateway |

| ∃x hasTemporalConstraint (Intervention, x) ⟶ ∃y hasTemporalConstraint (TemporalConstraint, y) |
| --- |
| ∃x hasVolumetricConstraint (Intervention, x) ⟶ ∃y hasVolumetricConstraint (VolumetricConstraint, y) |
| ∃x hasSequenceConstraint (Intervention, x) ⟶ ∃y hasSequenceConstraint (SequenceConstraint, y) |
| ∃x hasRoleConstraint (Intervention, x) ⟶ ∃y hasRoleConstraint (Role, y) |

FIG. 11

| Column | Description | Filling method |
| --- | --- | --- |
| Rule ID | Sequential number which uniquely identifies the rule | Sequence number |
| Task (Intervention) | Task name to which the compliance rule applies | Value "x" of first-order logic sentence |
| Deviation type | Defines the type of deviation which conformance rule will check | Flag assigned from the first predicate of first-order logic sentence. (i.e. "hasTemporalConstraint," "hasVolumetricConstraint," etc.) |
| Min value | Lower limit for assigning complicane | Value "y" of first-order logic sentence |
| Max value | Higher limit for assigning complicane | Value "y" of first-order logic sentence |
| Precedent task | Identification of the precedent task used in the conformance rules of sequence type | Value "y" of first-order logic sentence |
| Role | Authorized role to perform the task | Value "y" of first-order logic sentence |

| Rule ID | Task (Intervention) | Deviation type | Min value | Max value | Precedent task | Role |
|---|---|---|---|---|---|---|
| 01 | Administration of antibiotic | Time | 60 | 60 | | Nurse |
| 02 | Prescription of antibiotic | Role | | | | Physician |
| 03 | Administration of antibiotic | Sequence | | | Blood culture | Nurse |

FIG. 12

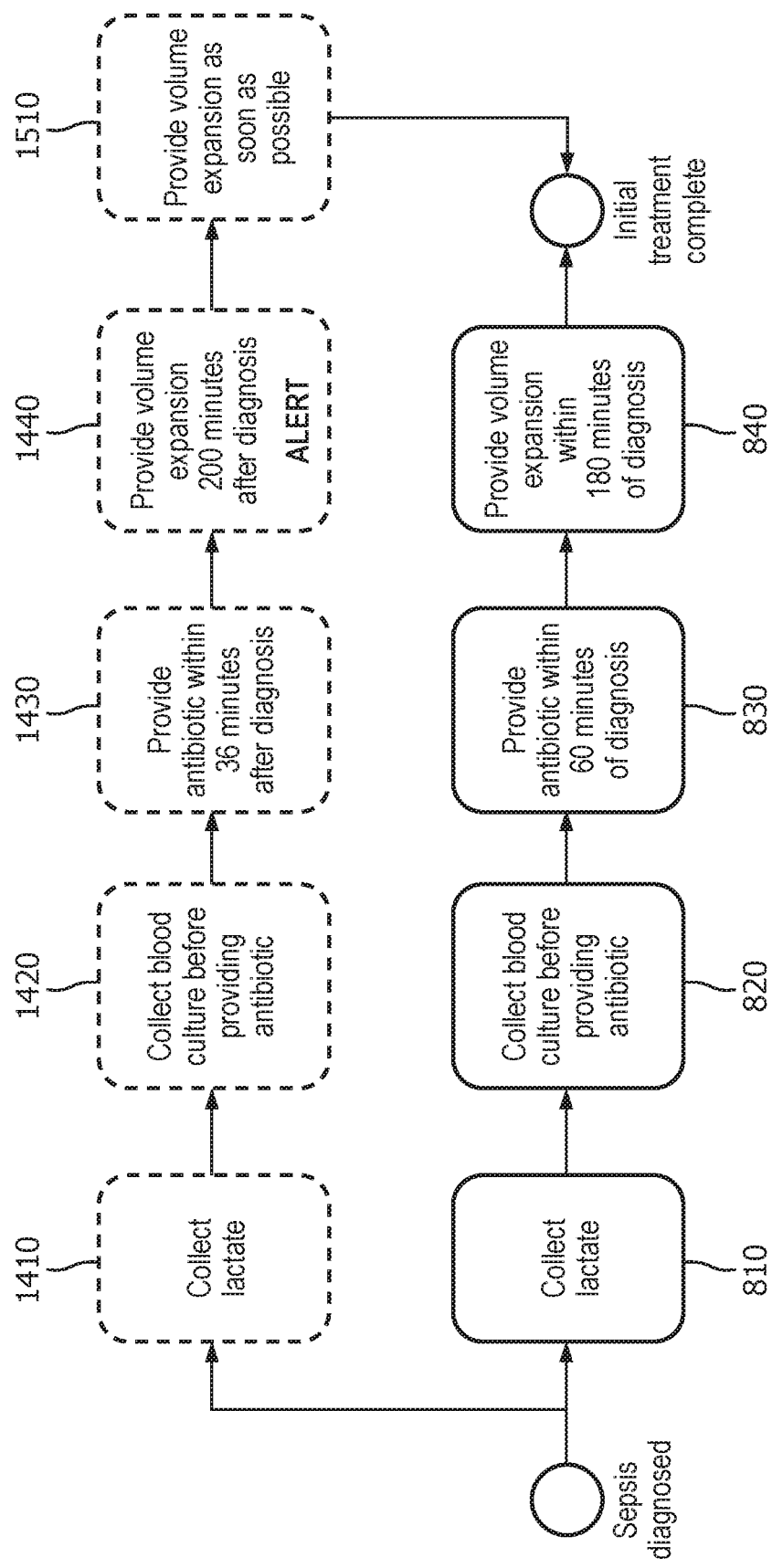

METHODS AND SYSTEMS FOR DEFINING CLINICAL PATHWAY DEVIATION RULES

FIELD OF THE DISCLOSURE

The present disclosure is directed generally to methods and systems for defining and using clinical pathway deviation rules in a clinical pathway management system.

BACKGROUND

A clinical pathway (CP), also known as a care pathway or clinical protocol, is a tool utilized in the healthcare system to standardize care, in part by minimizing variations in care and treatment procedures for a specific disease. A CP can also be described as a multidisciplinary management tool based on evidence-based practice for a specific group of patients with a predictable clinical course, in which the different tasks or interventions by the professionals involved in the patient care are defined, optimized and sequenced by intervals such as hour, day or visit.

Numerous studies have demonstrated that implementation of clinical pathways reduce variability and improve patient outcomes in many different healthcare settings. Despite studies showing the benefits of clinical pathway implementation, utilization of and compliance with clinical pathway systems is generally lower than desired or expected by healthcare quality analysts.

Clinical pathways management systems (CPMS) are software tools that implement clinical pathways and therefore assistant healthcare professionals adhere to these clinical pathways by identifying deviations in the workflow and emitting alerts to the healthcare professionals. Typically, identification of deviations is based on a set of rules which vary according to the protocol being utilized. The rules are typically created from clinical knowledge and institutional workflow. However, combining clinical knowledge into a workflow while providing flexibility in the creation of specific rules for each clinical pathway is a major challenge for clinical pathways management systems.

SUMMARY OF THE DISCLOSURE

There is a continued need for methods and systems that create deviation rules for clinical pathways, and alert users when a deviation in clinical treatment is identified. Various embodiments and implementations herein are directed to a method and system configured to create clinical pathway deviation rules using a semantic approach that combining clinical and workflow knowledge into an ontology representation, and extracts the rules from the ontology concepts and their relationships. The system comprises a reference ontology comprising information about execution of a plurality of clinical pathways. The system defines a domain ontology for one or more of these clinical pathways, comprising the addition of one or more subclasses about a specific disease or condition to one or more classes of the relevant reference ontology. At least some of the added subclasses include one or more deviation boundaries. The system converts the defined domain ontology for the specific disease to a graphical representation of an executable specific disease workflow, the executable specific disease workflow including a plurality of tasks. A rules generator creates one or more specific disease workflow deviation rules using the defined domain ontology for the specific disease. The system then receives, from an electronic medical record system (EMR), information about one or more treatment actions relative to a patient being treated for the specific disease. A rules executor then compares the received information with the one or more specific disease workflow deviation rules, and identifies any deviations in a treatment action. If there is a deviation in a treatment action, the system alerts the user of the clinical pathways management system to the identified deviation.

Generally, in one aspect, a method for alerting a user of a clinical pathways management system to a clinical pathway deviation is provided. The method includes: (i) providing a reference ontology comprising information about implementation of a plurality of clinical pathways; (ii) defining a domain ontology, wherein defining the domain ontology comprises adding one or more subclasses to one or more classes of the reference ontology, and further wherein each added subclass comprises one or more deviation boundaries; (iii) converting the domain ontology to one or more graphical representations of clinical pathways, wherein each clinical pathway comprises one or more interventions; (iv) generating, by a rules generator using the domain ontology, one or more deviation rules for a plurality of the clinical pathways; (v) receiving information about one or more interventions relative to a patient being treated using a first clinical pathway; (vi) identifying, by a rules executor comparing the received information about one or more interventions with the one or more deviation rules for the first clinical pathway, one or more deviations from the first clinical pathway; and (v) alerting, via an alert, the user of the clinical pathways management system to the identified one or more deviations from the first clinical pathway.

According to an embodiment, the method further includes the step of storing information about the identified one or more deviations from the first clinical pathway.

According to an embodiment, the method further includes the step of modifying, in response to the received alert and the identified one or more deviations from the first clinical pathway, one or more interventions for the patient.

According to an embodiment, the method further includes the step of discarding the received information about one or more interventions relative to a patient being treated using a first clinical pathway, if the received information is missing a timestamp or personnel identification.

According to an embodiment, the alert comprises a display of the identified one or more deviations in a graphical representations of the first clinical pathway. According to an embodiment, the alert comprises an identification of where in the first clinical pathway the identified one or more deviations occurred.

According to an embodiment, the system is configured generate deviation rules using first order logic, translate the deviation rules into an if-then-else format, and store the if-then-else format in a database.

According to an embodiment, the reference ontology is based at least in part on a plurality of clinical reports relevant to a plurality of clinical pathways.

According to an embodiment, the deviation rules comprise temporal constraints, sequential constraints, volumetric constraints, and/or professional role constraints.

According to an embodiment, the domain ontology is converted to one or more graphical representations of clinical pathways using Business Process Model and Notation (BPMN).

According to another aspect is provided a system configured to alert a user to a clinical pathway deviation. The system includes a reference ontology comprising information about implementation of a plurality of clinical pathways; a domain ontology, comprising one or more subclasses added to one or more classes of the reference ontology, and wherein each subclass comprises one or more deviation boundaries; and a processor configured to: (i) convert the domain ontology to one or more graphical representations of clinical pathways, wherein each clinical pathway comprises one or more interventions; (ii) generate, using the domain ontology, one or more deviation rules for a plurality of the clinical pathways; (iii) receive information about one or more interventions relative to a patient being treated using a first clinical pathway; (iv) identify, by comparing the received information about one or more interventions with the one or more deviation rules for the first clinical pathway, one or more deviations from the first clinical pathway; and (v) alert, via an alert, the user of the clinical pathways management system to the identified one or more deviations from the first clinical pathway.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. The figures showing features and ways of implementing various embodiments and are not to be construed as being limiting to other possible embodiments falling within the scope of the attached claims. Also, the drawings are not necessarily to scale, emphasis instead generally being placed upon illustrating the principles of the various embodiments.

FIG. 7 is a table mapping a conceptual model to a workflow model, in accordance with an embodiment.

FIG. 10 is a table demonstrating first-order logic sentences, in accordance with an embodiment.

FIG. 11 is a table of relational database columns and the process for filling the columns, in accordance with an embodiment.

FIG. 12 is an example table of filled relational database columns, in accordance with an embodiment.

FIG. 15 is a graphical representation of an executable clinical pathway workflow comprising interventions/tasks, in accordance with an embodiment.

DETAILED DESCRIPTION OF EMBODIMENTS

Figure 1:
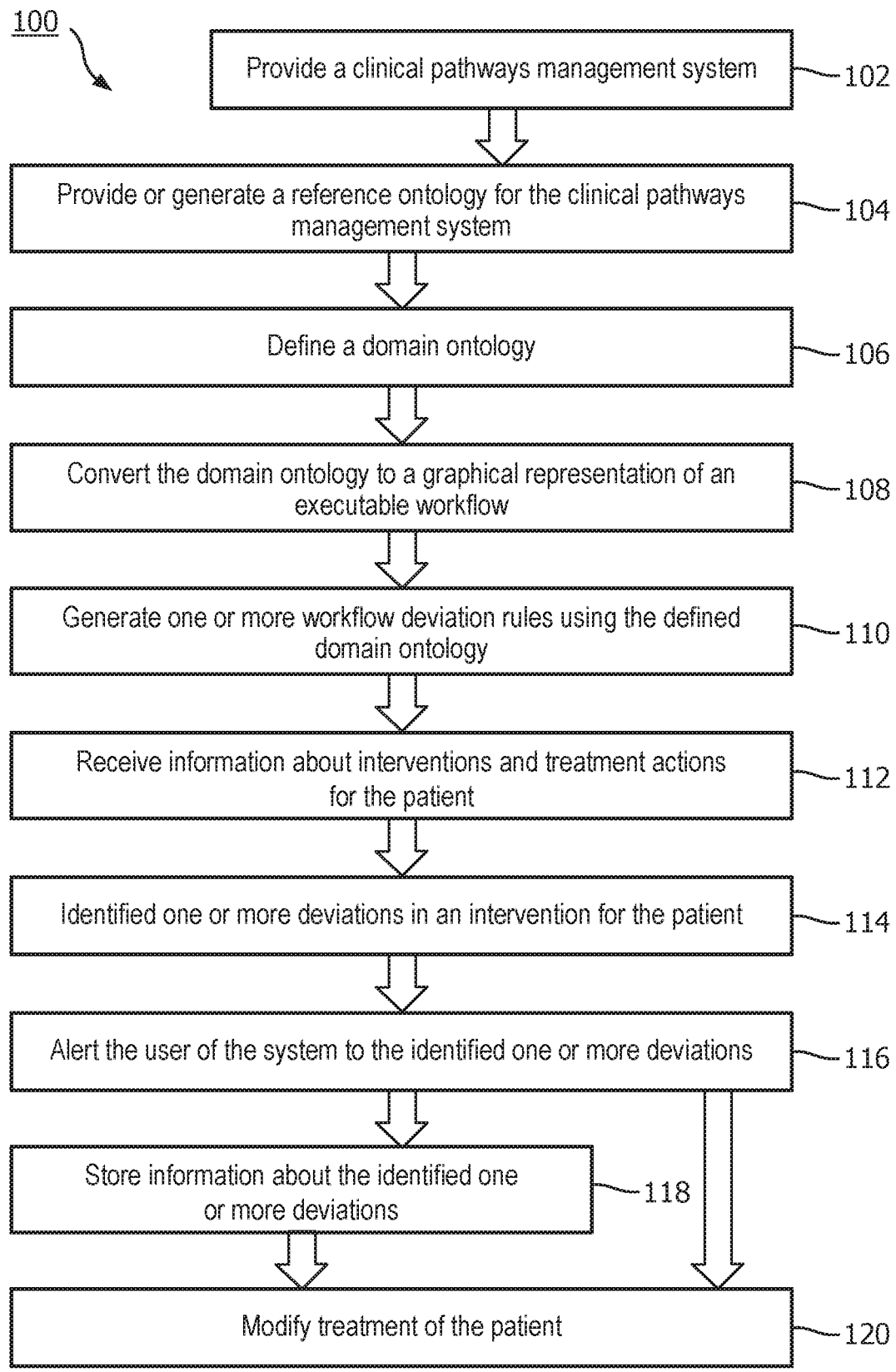
FIG. 1 is a flowchart of a method for alerting a user of a clinical pathways management system to a clinical pathway deviation, in accordance with an embodiment.

The present disclosure describes various embodiments of a system and method configured to alerting a user of a clinical pathways management system to a clinical pathway deviation. More generally, Applicant has recognized and appreciated that it would be beneficial to provide a method and system to alert healthcare professionals to care deviations. The system comprises a reference ontology comprising information about execution of a plurality of clinical pathways. The system defines a domain ontology for one or more of these clinical pathways, comprising the addition of one or more subclasses about a specific disease or condition to one or more classes of the relevant reference ontology. At least some of the added subclasses include one or more deviation boundaries. The system converts the defined domain ontology for the specific disease to a graphical representation of an executable specific disease workflow, the executable specific disease workflow including a plurality of tasks. A rules generator creates one or more specific disease workflow deviation rules using the defined domain ontology for the specific disease. The system then receives, from an electronic medical record system (EMR), information about one or more treatment actions relative to a patient being treated for the specific disease. A rules executor compares the received information about one or more treatment actions with the one or more specific disease workflow deviation rules, and identifies any deviations in a treatment action. If there is a deviation in a treatment action, the system alerts the user of the clinical pathways management system to the identified deviation.

In certain embodiments, healthcare professionals use information about clinical pathway deviations provided by the clinical pathways management system for treatment of a patient. For example, identification of a clinical pathway deviation by the system via an alert or other notification method can not only prevent errors or unwanted/unnecessary treatment, but can cause the healthcare professional to modify a patient's care. The healthcare professional may utilize the information about the deviation to act in the task that led to the deviation, such that there is no longer a deviation. Alternatively, the healthcare professional may treat the patient in another way to rectify or obviate the deviation or effects of the deviation. Many other responding effects resulting from the identification of a deviation are possible.

Accordingly, the methods and systems described or otherwise envisioned herein generate clinical pathway deviation rules using a semantic approach that combining clinical and workflow knowledge into an ontology representation and extract the rules from the ontology concepts and their relationships.

In certain embodiments, healthcare institutions use information about clinical pathway deviations provided by the clinical pathways management system to analyze or evaluate care at that institution. For example, the institution may gather statistics for deviations by an individual, a department, a treatment, a patient, an organization, and/or at many other levels or groupings. This may help the institution identify problem areas such as individuals, departments, treatments, and more. The institution may then be able to address the problem area utilizing the informative deviation analysis provided by the clinical pathway management system.

In certain embodiments, the systems and methods described herein combine two different types of knowledge, clinical and workflow knowledge, to create clinical pathway deviation rules. Additionally, the systems and methods enable a flexible framework that does not require change in source code to include new rules or to update existing rules, and ensure flexibility in creating rules for different protocols.

The embodiments described or envisioned herein provide a system and method that combines and workflow knowledge in an ontology format for creating and managing clinical pathways. This approach improves upon previous approaches in many ways. For example, one aim of the method is to translate semantic rules encoded in an Ontology Web Language (OWL) format into if-then-if statements stored in a database table, in order to simplify the implementation of those rules in an EMR, thus avoiding the integration of several components at runtime. Additionally, the method focuses specifically on the identification of deviations in the execution of the clinical pathway, while the most previous approaches focus on the selection of a subprocess within the workflow.

Further, unlike previous approaches, the method and system described or envisioned herein do no encode the rules in Semantic Web Rule Language (SWRL) or another formal language. Instead, the current approach uses only concepts and their relationships. Accordingly, the process of ontology modelling becomes easier since a professional trained in SWRL is not required. Similarly, the current approach does not require a reasoning engine such as JESS or similar. This means more simplicity and more performance, since the rules as if-then-else statements will be stored in a local database and will not require any data loading or transformation. The present approach does not require any additional mechanism for data security, since no data interchange is performed. This is yet another improvement over existing approaches where EMR data must instantiate the rules encoded inside ontology.

Referring to FIG. 1, in one embodiment, is a flowchart of a method 100 for alerting a user of a clinical pathways management system to a clinical pathway deviation. The methods described in connection with the figures are provided as examples only, and shall be understood not to limit the scope of the disclosure. The clinical pathways management system can be any of the systems described or otherwise envisioned herein.

Figure 2:
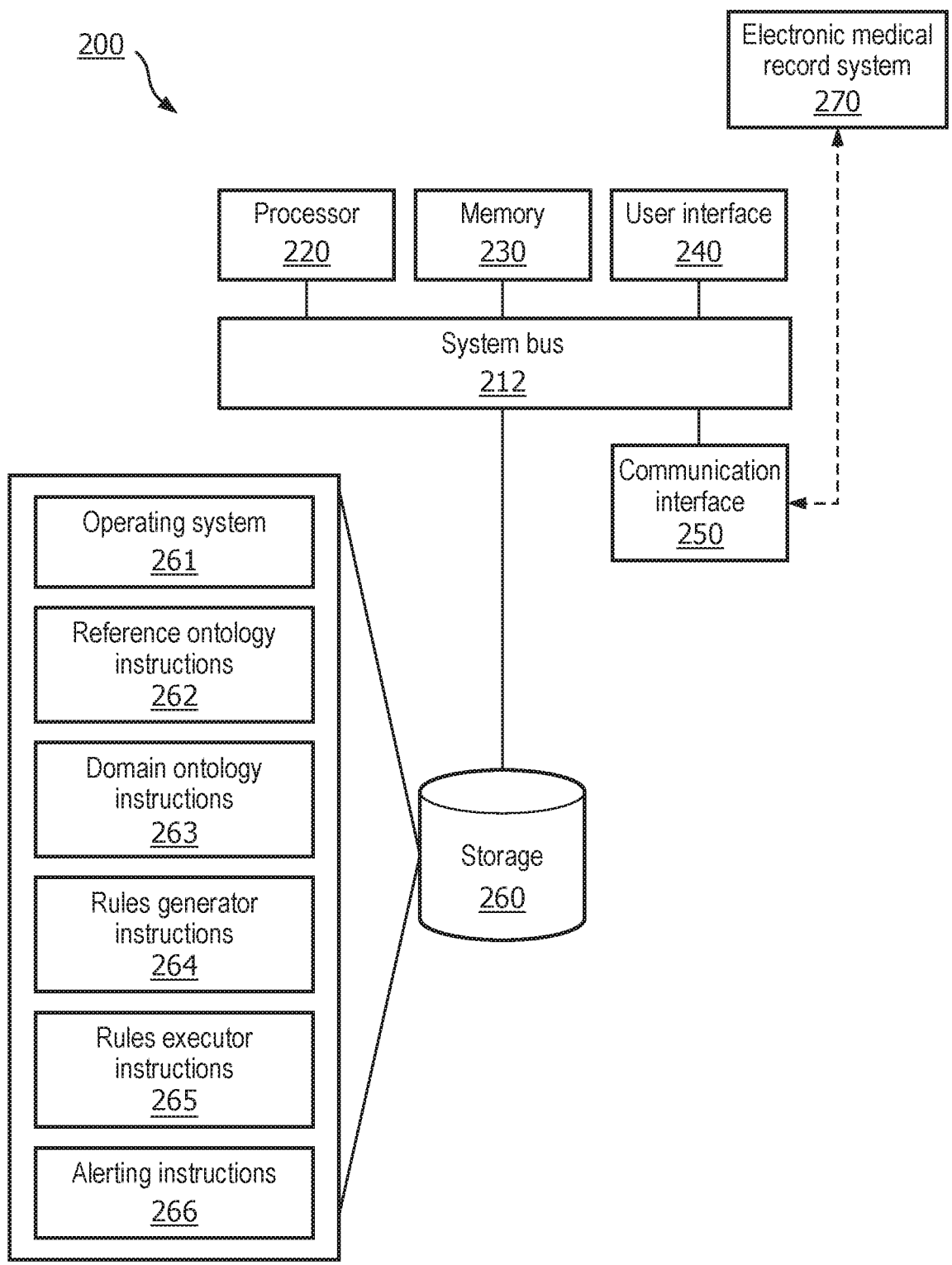
FIG. 2 is a schematic representation of a clinical pathways management system, in accordance with an embodiment.

At step 102 of the method, according to an embodiment, a clinical pathways management system 200 is provided. Referring to an embodiment of a clinical pathways management system 200 as depicted in FIG. 2, for example, the system comprises one or more of a processor 220, memory 230, user interface 240, communications interface 250, and storage 260, interconnected via one or more system buses 212. It will be understood that FIG. 2 constitutes, in some respects, an abstraction and that the actual organization of the components of the system 200 may be different and more complex than illustrated. Additionally, clinical pathways management system 200 can be any of the systems described or otherwise envisioned herein.

Figure 3:
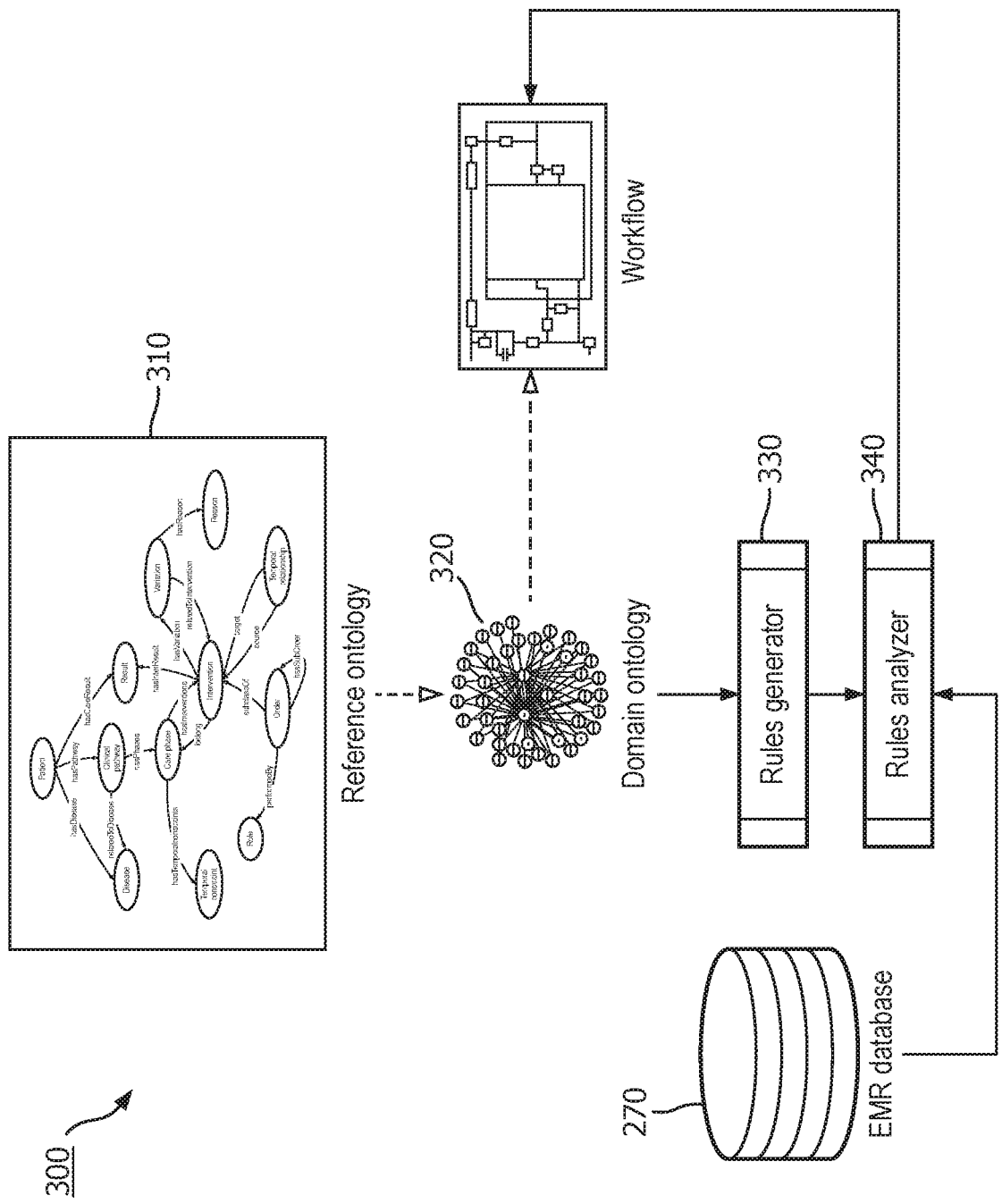
FIG. 3 is a flowchart of a method for a clinical pathways management system to identify a clinical pathway deviation, in accordance with an embodiment.

Referring to FIG. 3, in one embodiment, is a flowchart of a method 300 for alerting a user of a clinical pathways management system to a clinical pathway deviation, similar to the method shown in FIG. 1 and described below. The method includes a reference ontology 310, a domain ontology 320, a rules generator 330, a rules analyzer 340, and an electronic medical record (EMR) system 270 containing electronic health records or electronic medical records for one or more patients.

At step 104 of the method, according to an embodiment, a reference ontology 310 comprising information about execution of a plurality of clinical pathways is provided. The clinical pathway reference ontology represents a meta-level conceptual model. According to an embodiment, the reference ontology provides a conceptual representation for a typical clinical pathway, which is usually a process consisting of multiple care phases. Each phase is associated with information such as a set of temporal constraints, which can include start time, expire time, and duration. According to an embodiment, the reference ontology comprises different classes and/or other methods of organization of properties and relations between data.

The reference ontology 310 may be provided by or obtained from any source. As just one example, the reference ontology may be derived from a plurality of clinical reports or other medical data that is electronic or has been digitized. Information is extracted from the reports or data using traditional means and is organized to form the reference ontology. Accordingly, the reference ontology 310 is defined at least in part by the plurality of clinical reports or other medical data utilized to create that reference ontology, and thus the reference ontology of a first clinical pathways management system 200 at a first location, installation, or facility can or will be different than the reference ontology of a second clinical pathways management system 200 at a second location, installation, or facility. According to an embodiment, the reference ontology can be stored in memory.

Figure 4:
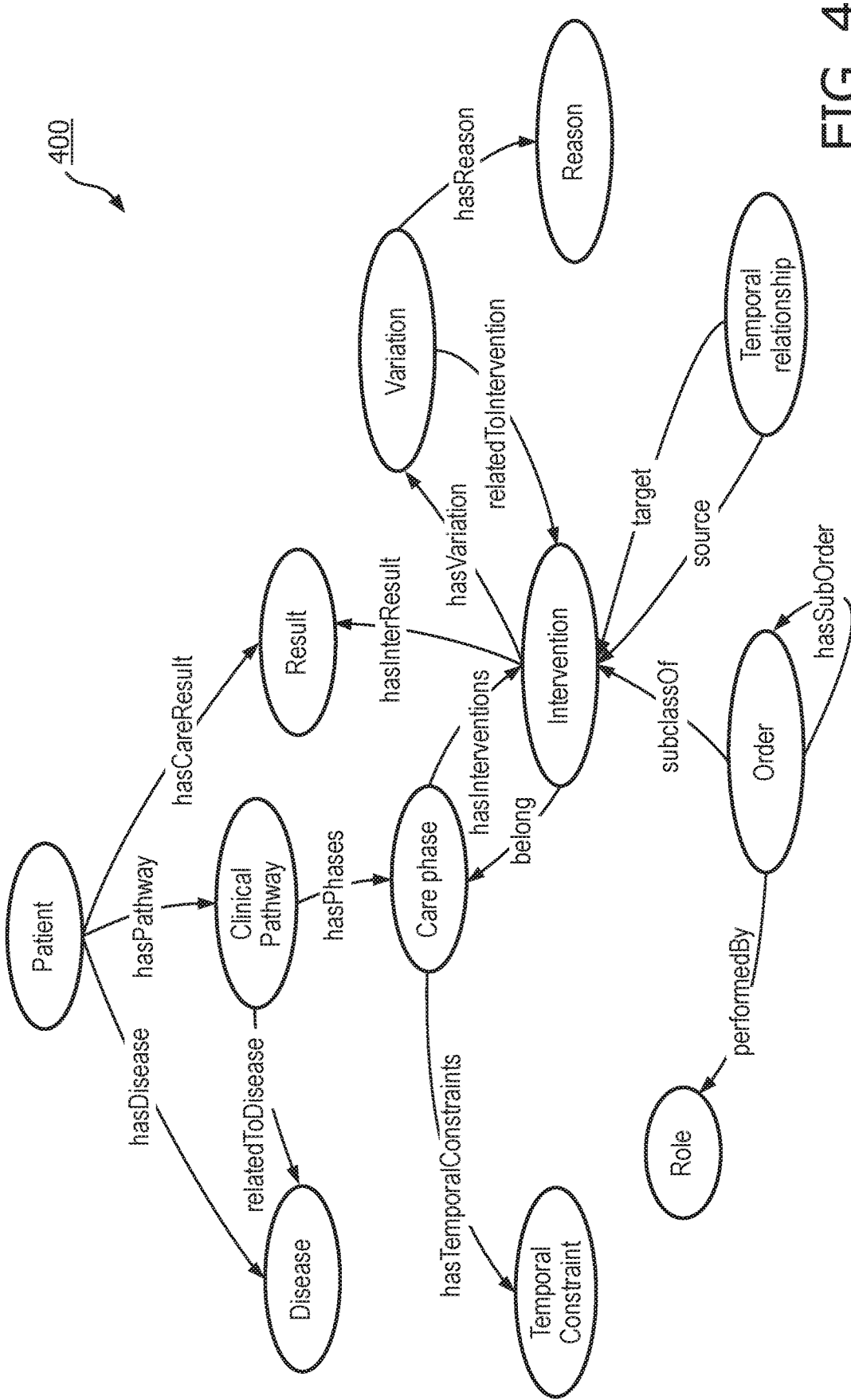
FIG. 4 is a meta-level conceptual representation for clinical pathways, in accordance with an embodiment.

According to an embodiment of a CPMS reference architecture, there is a meta-level conceptual representation 400 for clinical pathways as shown in FIG. 4. A conceptual representation for a typical clinical pathway can be a process consisting of multiple care phases, where each phase is associated with a set of temporal constraints, such as start time, expire time, and duration, among others. To arrive at a more useful architecture, several concepts were added to produce the CP reference ontology described herein.

For example, the concept of 'Result' in FIG. 4 was extended by inclusion of some additional subclasses in order to categorize the different kind of the results. For example, subclasses such as 'Discharge', 'Death', and others were included to identify whether a result is an outcome of the patient or the intervention.

Similarly, the concept 'Intervention Kind' was included to specify the different categories of intervention (actions) in the workflow. According to an embodiment it can be very important to analyze the pathway deviations considering these categories, as each is related to different departments in the hospital and to different professional skills. According to an embodiment, the categories of 'Intervention kind' can be 'Medical Prescription,' 'Medical Evaluation,' 'Administrative Action,' 'Transportation Action,' and 'Communication Action,' among many other possibilities.

Another addition to the conceptual model was the inclusion of subclasses to categorize the deviations in different types. Thus, it is possible to analyze the pathway conformance according to 'Target Time,' 'Target Order,' 'Target Volume,' and 'Target Role,' among many other possibilities.

Additionally, included are other classes to represent additional constraints that can be used to consider to identify pathway deviations, such as 'Sequence Constraint' and 'Volumetric Constraint,' among many other possibilities.

Notably, this description of the classes, subclasses, and organizational structure are provided only as possible non-limiting embodiments of the method and system. Other classes, subclasses, and relationships can be utilized in the reference ontology.

Figure 5:
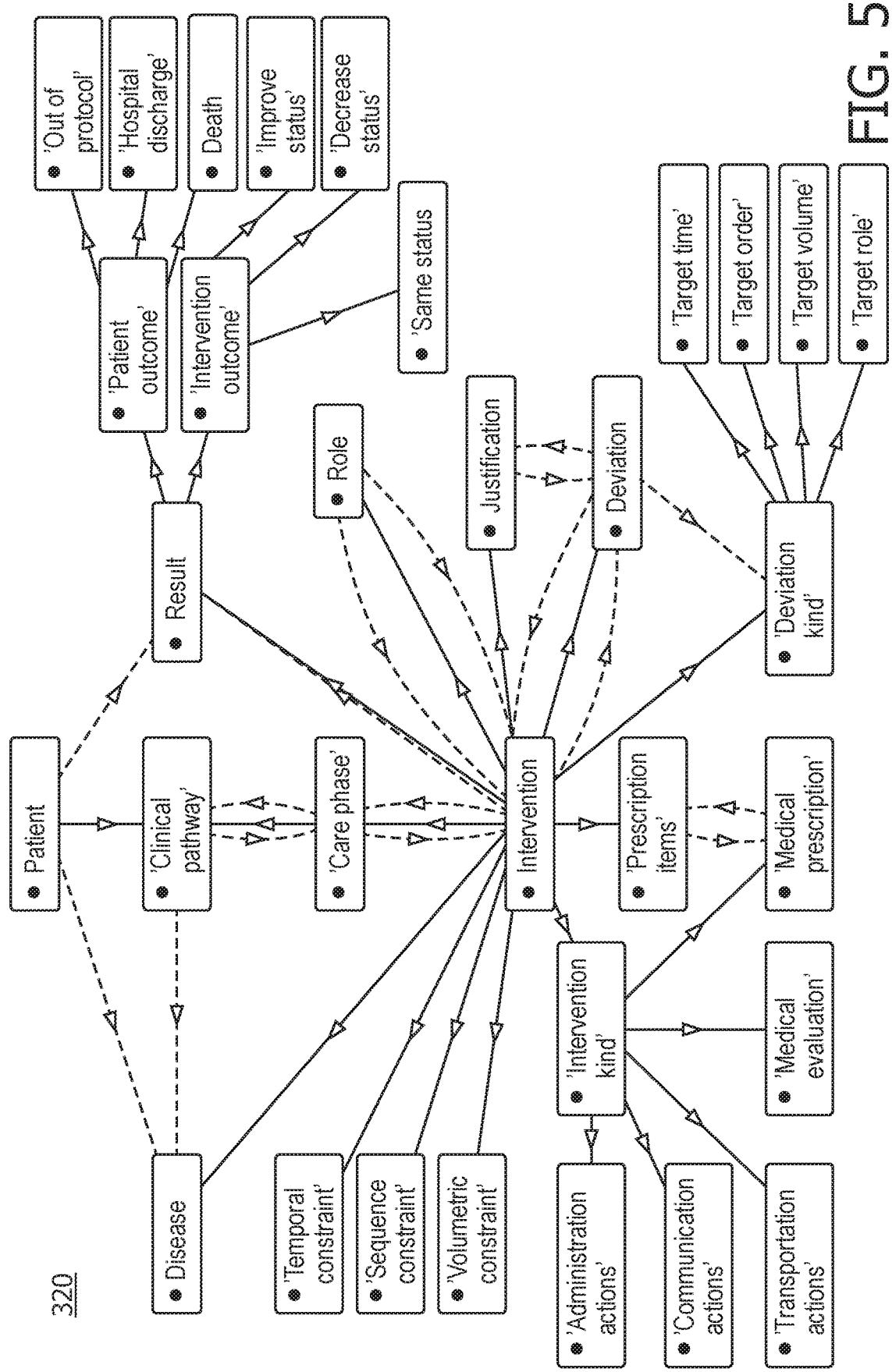
FIG. 5 is a schematic representation of a reference ontology, in accordance with an embodiment.

Referring to FIG. 5, in one embodiment, is a chart depicting an expanded clinical pathway reference ontology 320 which has been expanded by defining domain ontology. The expanded clinical pathway reference ontology comprises classes such as "Intervention," "Patient," "Disease," and others.

At step 106 of the method, according to an embodiment, a domain ontology 320 for one or more of the clinical pathways utilized or monitored by the clinical pathways management system is defined by the system. According to an embodiment, defining a domain ontology comprises adding one or more subclasses about a specific disease or condition to one or more classes of the relevant reference ontology. One or more of the subclass may comprise information about one or more deviation boundaries. The subclasses are related to a specific protocol. Domain ontology for each specific CP should be developed from the reference ontology. According to an embodiment, subclasses related to the specific protocol into the classes of reference ontology. Using a defined sepsis treatment as an example, subclasses are added to the "Interventions" class in the reference ontology that correspond to the interventions defined in the sepsis protocol. The sepsis treatment subclasses in the domain ontology corresponding to the "Interventions" class in the reference ontology could be, for example, 'Lactate Request' and/or 'Blood Culture Request,' among many others.

According to another embodiment, annotation properties, also called features of objects, are included in the domain ontology to facilitate the formation of deviation rules. For example, properties such as "TaskID," "TasksFlow," "DecisionGate," "EvaluationClass," and "Abnormal Values," among many others, can be added to define the order of tasks.

According to an embodiment, "TaskID" property is a numeric identification assigned to classes related to interventions of clinical protocol. This can facilitate the generation of the BPMN representation of clinical workflow through a domain ontology, as discussed below.

According to an embodiment, "TasksFlow" is a property filled out only to "Care Phase" class in order to indicate the sequence of interventions (TaskIDs) which belongs to that treatment phase.

According to an embodiment, the "DecisionGate" property is used to indicate whether that class is an intervention task that can decide a change of way in the workflow. This property can be used together with properties such as "EvaluationClass" and "AbnormalValues". For example, the class "Infection Confirmation" can be addressed as a decision gate, which will cause a change of pathway flow. This change of route will happen by existence of abnormal values ("Abnormal Values") in an evaluation class ("EvaluationClass").

Figure 6:
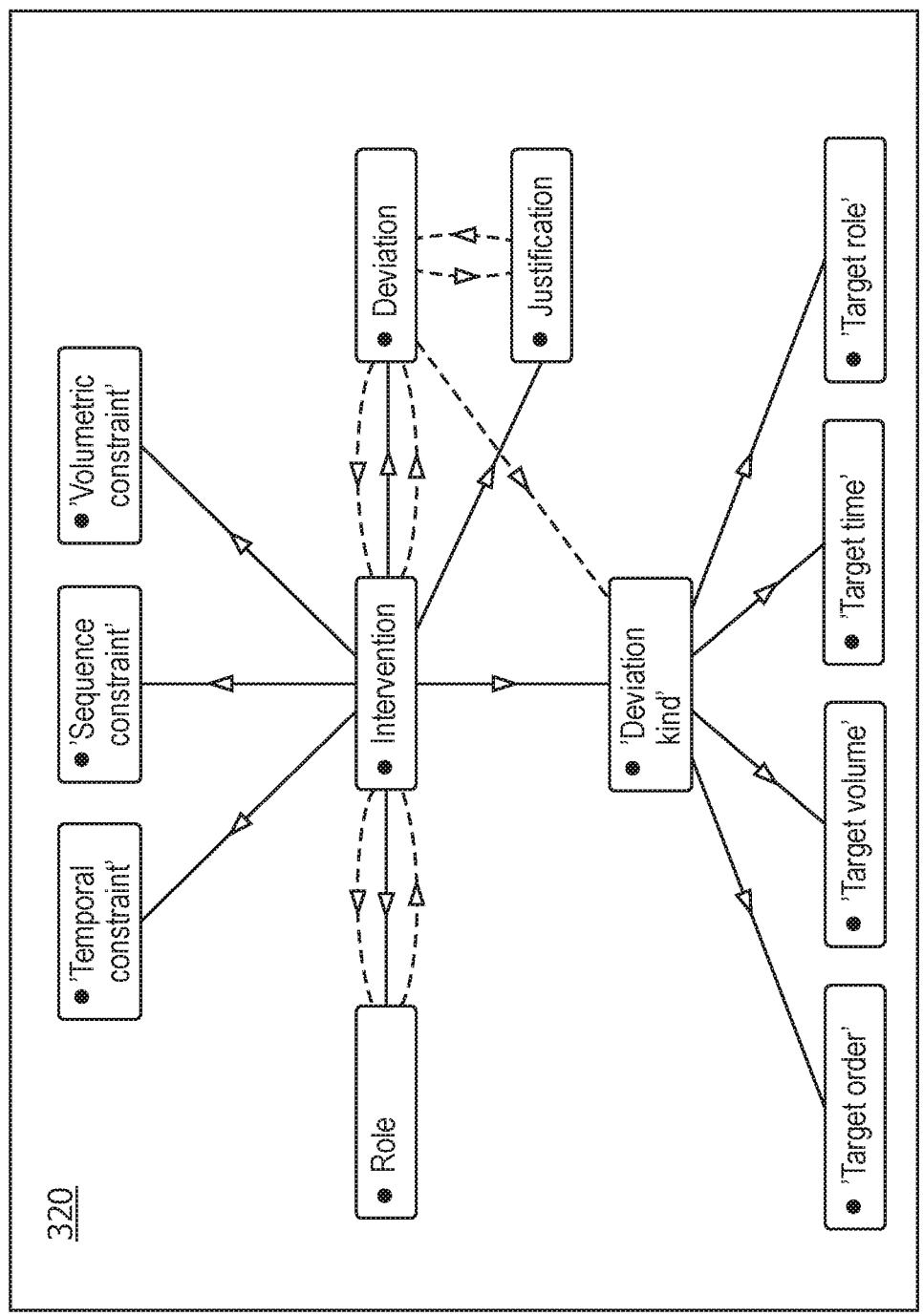
FIG. 6 is a schematic representation of a domain ontology, in accordance with an embodiment.

Of upmost importance for identifying deviations in treatment are the classes related to deviation identification (such as those as shown in FIG. 6 described below), because it is from these classes and their relationships that rule deviations are determined or inferred.

According to an embodiment, each intervention is restricted by a constraint based on a target. Constraints can be temporal, sequential, or volumetric, among other options. A deviation occurs when an intervention is performed out of constraint established, for example, if an intervention was executed out of time defined by temporal constraint class.

The "Role" class also is used in the deviation identification process. A deviation can occur, for example, if an intervention is executed by a role different from that assigned to that intervention, such as when one professional performs the task assigned to another professional.

Referring to FIG. 6, in one embodiment, is a representation of a domain ontology 320. The domain ontology comprises the logic for identifying pathway deviations. Each task (such as "Intervention") of a clinical pathway is restricted by one or more constraints that are used to define deviations. An action or intervention that exceeds the constraint for a task, or otherwise operates outside a task constraint, may be defined as a deviation. According to an embodiment, examples of constraints include temporal constraints, sequential constraints, volumetric constraints, and/or professional role constraints, among many other types of constraints.

According to an embodiment, the reference values for constraints are defined by instances of classes. A temporal constraint for a task is typically a period of time utilized in a clinical pathway. As just one example, a temporal constraint may be to provide a first dose of an antibiotic, during sepsis treatment, within sixty minutes of the diagnosis. The class "Temporal Constraint" in ontology 320 can have instances of "60 minutes," "30 minutes," "one day," and many other examples.

A sequential constraint for a task is typically a specific order of actions within a clinical pathway. As just one example, a sequential constraint may be to provide the patient with antibiotic A prior to providing the patient with antibiotic B. The class "Sequential Constraint" in ontology 320 can have instances of "antibiotic A before antibiotic B" or "antibiotic C before medicine Z," among many other examples.

A volumetric constraint for a task is typically an amount or dosage of a treatment provided to a patient within a clinical pathway. As just one example, a volumetric constraint may be to provide the patient with 100 ml of antibiotic A. The class "Volumetric Constraint" in ontology 320 can have instances of "100 ml of antibiotic A" or "only 250 mgs of antibiotic B within 24 hours," among many other examples.

A professional role constraint for a task is typically a requirement that a specific healthcare professional perform a specific task or analysis. As just one example, a professional role constraint may be that only a licensed physician or registered nurse can provide narcotic J to a patient within a clinical pathway. As another example, a role constraint may be that only a physician previously assigned to a patient can change a treatment protocol for the patient. The class "Role Constraint" within ontology 320 can have instances of "only physician John Doe can modify treatment" or "a licensed physician or registered nurse can prescribe narcotic J," among many other examples.

At step 108 of the method, according to an embodiment, at least a portion of the defined domain ontology is converted to a graphical representation of an executable workflow comprising one or more tasks. For example, a defined domain ontology for a specific disease can be converted to a graphical representation of an executable clinical workflow for that specific disease, and the workflow will comprise one or more tasks relevant to the specific disease. Thus the system may comprise a graphical representation of an executable clinical workflow or treatment plan for the disease, with the graphical representation comprising one or more specific treatment or analytical tasks relevant to a disease treatment workflow.

According to an embodiment, therefore, a pathway can be represented as an overall process consisting of multiple sub-processes representing care phases, where each phase can be further specified as tasks in a sub-process.

Referring to FIG. 7, in one embodiment, is a table 700 showing the mapping of a conceptual model to a workflow model in order to generate a graphical representation of an executable workflow. For example, a clinical pathway in the system ontology is a process in the workflow model, an intervention is an order, and clinical data gathered during or after an intervention is data output. Thus, FIG. 7 depicts the basic mapping of domain ontology concepts to an executable workflow models that can be supported by a general purpose workflow engine. In a general view, a pathway is represented as an overall process consisting of multiple sub-processes representing care phases. Each phase is further specified as tasks in the sub-process.

According to an embodiment, the graphical representation used to depict a clinical pathway as a process is any model that successfully generates and provides an acceptable graphical representation. One example of a graphical representation is Business Process Model and Notation (BPMN), although other implementations are possible.

Figure 8:
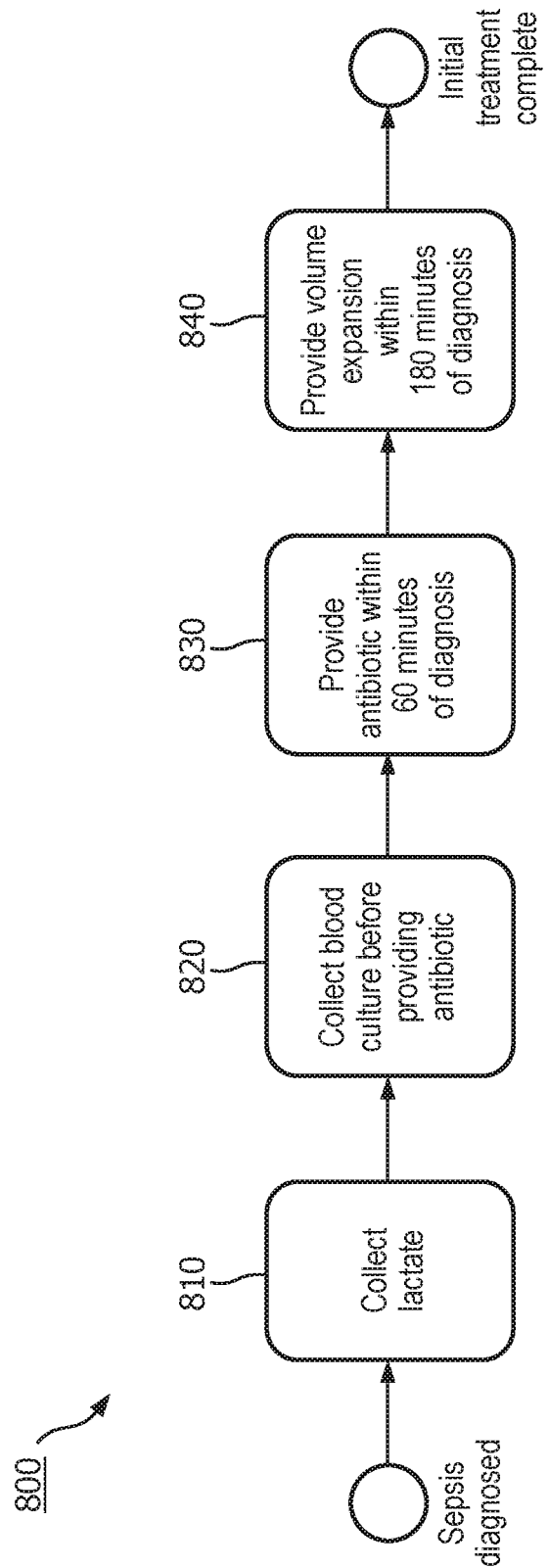
FIG. 8 is a graphical representation of an executable clinical pathway workflow comprising interventions/tasks, in accordance with an embodiment.

Referring to FIG. 8, in one embodiment, is an example of a graphical representation 800 of an executable workflow comprising tasks 810 through 840. In this non-limiting example, the physician diagnoses a patient with sepsis, thereby beginning a specific clinical pathway for initial sepsis treatment. The next step in the clinical pathway is to collect lactate at 810. Next, the physician collects a blood culture before providing an antibiotic at 820. The physician must now provide an antibiotic within 60 minutes of the sepsis diagnosis at 830. At 840, the physician must provide a volume expansion with 180 minutes of the sepsis diagnosis. Although this clinical pathway includes only two tasks, some clinical pathways may comprise tens or hundreds of tasks.

At step 110 of the method, according to an embodiment, the system generates one or more workflow deviation rules using the defined domain ontology. According to an embodiment, a rules generator or rules generator instructions 264 of the clinical pathways management system 200 generates workflow deviation rules from concepts and instances of ontology. As described herein, the rules generator utilizes the one or more constraints associated with an intervention or task to generate workflow deviation rules. For example, an intervention may comprise temporal constraints, sequential constraints, volumetric constraints, and/or professional role constraints, among many other types of constraints. The deviation rules created by the rules generator may use these constraints to define the boundaries or thresholds for the rules.

According to an embodiment, the methods and systems described or otherwise envisioned herein infer conformance rules encoded in a domain ontology and translate to if-then-if statements, which are stored in a relational database table and executed by the Rules Executor component in order to identify pathway deviations. As shown in FIG. 6, pathway conformance rules can be inferred from relationships between instances of domain ontology classes.

Figure 9:
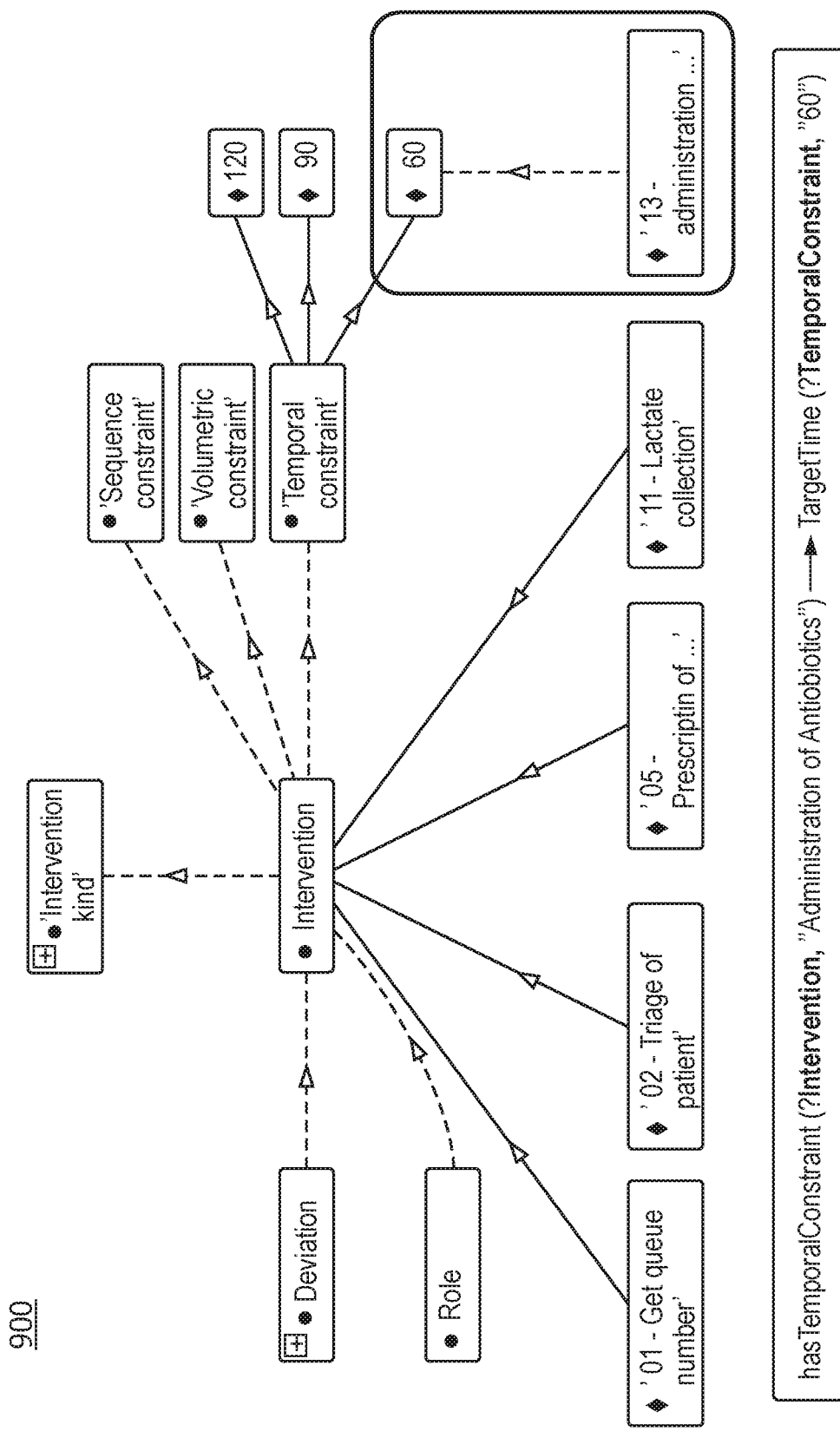
FIG. 9 is a representation of a temporal constraint rule, in accordance with an embodiment.

Referring to FIG. 9, according to an embodiment, is an example of a temporal constraint rule 900 defining 60 minutes for an antibiotic administration task. This rule can be inferred by the relationship of an instance of the class "Intervention" (e.g., Administration of Antibiotics) with a specific instance of class "TemporalConstraint" (e.g., 60).

Each relationship between two instances of the ontology is transformed into a rule in the first-order logic format, and then that formal expression is translated into an if-then-else statement that will be executed by the system, such as by the Rules Executor component. First-order logic allows the method or system to represent facts of reality (predicates) that imply other facts. The example presented in Eq. 1 shows that if a fact "A" occurs to an object "x" then the fact "B" is also true to object "y".

$$\exists x\ \text{FactA}(x) \exists y\ \text{FactB}(y) \qquad \text{Eq. 1}$$

In this way, the method or system can infer first-order logic sentences from the domain ontology using of classes instances and their relationships, to represent the pathways conformance rules. The table in FIG. 10, for example, shows four possible types of sentences that can be built, one for each of four deviation types. Other deviation types and types of sentences are possible. According to an embodiment, "x" is the instance of class "intervention" which is constrained by conformance rule, and "y" is the instance of the respective constraint class and "hasTemporalConstraint," "hasVolumetricConstraint," "hasSequenceConstraint," and "hasRoleConstraint" are the ontology properties that define the relationship between the instances.

According to an embodiment, the conformance rules inferred from domain ontology produce a relational database table that is used by the system, such as by a Rules Executor component, to identify the pathway deviations. FIG. 11 includes a table describing the database columns in the relational database table, and the method to filling them, and FIG. 12 includes an example table of comprising filled database columns, in accordance with an embodiment.

At step 112 of the method, according to an embodiment, the clinical pathways management system 200 receives information about a treatment or condition of the patient. For example, the system may be in communication with an electronic medical record (EMR) system 270 that contains electronic health records or electronic medical records for one or more patients. The health records can comprise any information about the patient, including identity, demographics, diagnosis, test results, medical history, and much more.

Pursuant to an embodiment of the method, a clinical pathway has been initiated for a patient and the patient's medical records are updated in the EMR system as each task/intervention is implemented, and/or as normally updated. For example, the patient's medical records can be updated with treatments, vitals, and/or any other events or information. Alternatively, information can be recorded in the patient's medical records if a task/intervention in the identified clinical pathway is not implemented.

Accordingly, the clinical pathways management system 200 receives information about implementation of the clinical pathway which can be utilized to identify adherence and/or non-adherence to the clinical pathway. Specifically, the system can utilize the EMR information to identify deviations from the implemented clinical pathway.

According to an embodiment, the clinical pathways management system retrieves data from an EMR. For example, the system or method may comprise an Executer module responsible for retrieving data from the EMR, identifying deviations in the clinical pathway execution, and/or presenting them to a user via a User Interface (UI) or other method.

Figure 13:
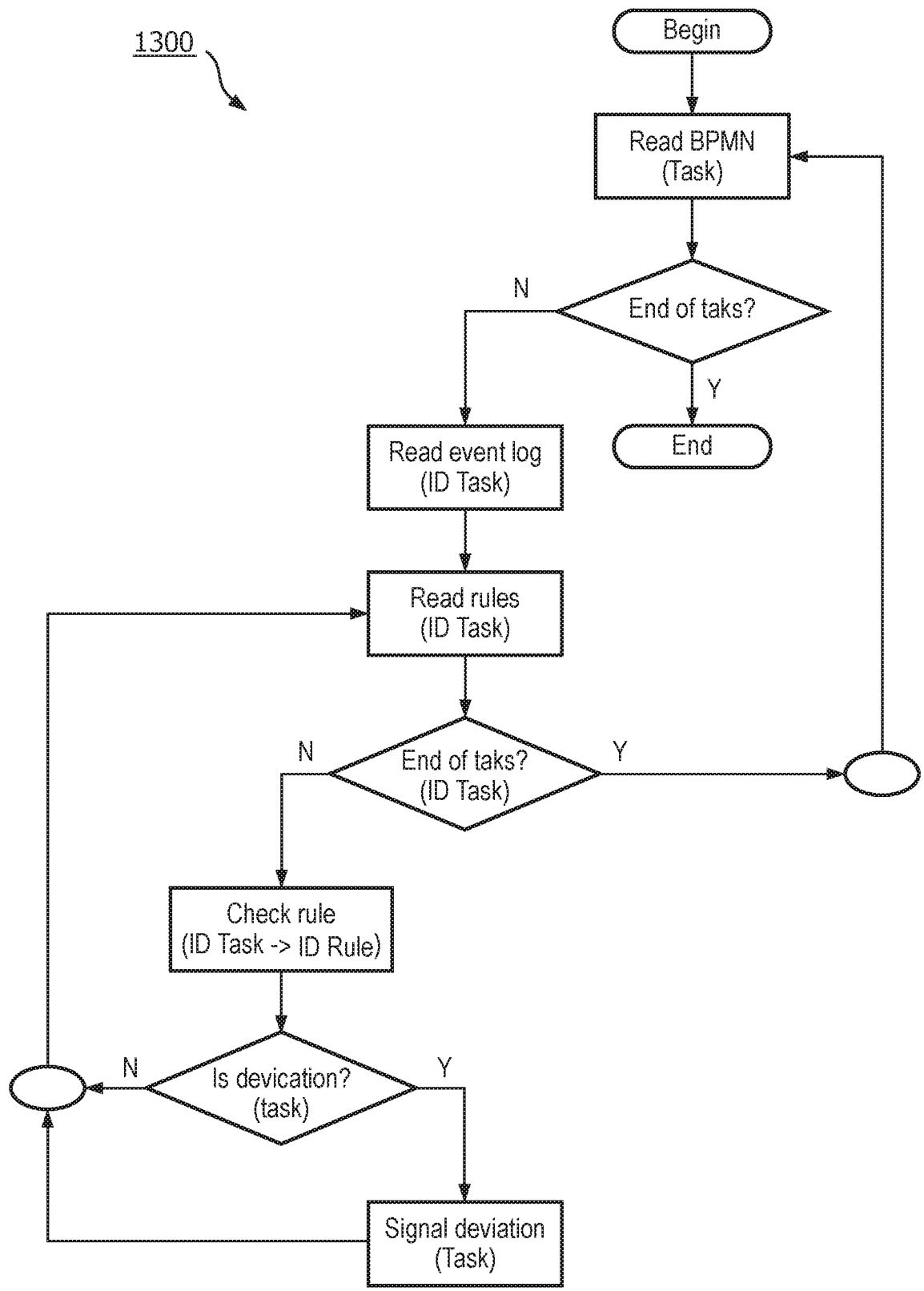
FIG. 13 is an algorithm for deviation identification, in accordance with an embodiment.

Referring to FIG. 13, in one embodiment, is an algorithm 1300 for deviation identification. For each BPMN task, the EMR data previously stored in an event log is retrieved. In addition, the database columns (Table shown in FIG. 11) related to conformance rules for that task are retrieved. Next, the system determines whether the EMR data meets the criteria of the conformance rules through if-then-else statements which compare these values with the one of the columns of the conformance rule ("Min value," "Max value," "Precedent Task," "Role," etc.) according to deviation type of error. If a deviation is identified it can be stored, presented such as via a UI, or otherwise noted.

At step 114 of the method, according to an embodiment, the system identifies one or more deviations in a task/intervention and/or in an implemented clinical pathway. The system identifies a deviation by comparing the received EMR information, and specifically the performed (or unperformed) task(s)/intervention(s) to the generated rules, and determines whether a rule or constraint has been violated or exceeded. According to an embodiment, a rules executor or rules executor instructions 265 of the clinical pathways management system 200 compares the received EMR information to the clinical workflow to identify deviations.

According to an embodiment, the identified deviation includes information about the deviation type and/or other information including but not limited to deviation type, workflow task/intervention, professional role, work shift and date/time of intervention, and/or any other information.

The rules executor or rules executor instructions 265 receives data from EMR related to the care actions for that patient, which are flagged into the clinical pathway workflow. The rules executor can show the patient's status in the workflow graphical representation and can detect if any deviations have occurred in the clinical pathway.

Figure 14:
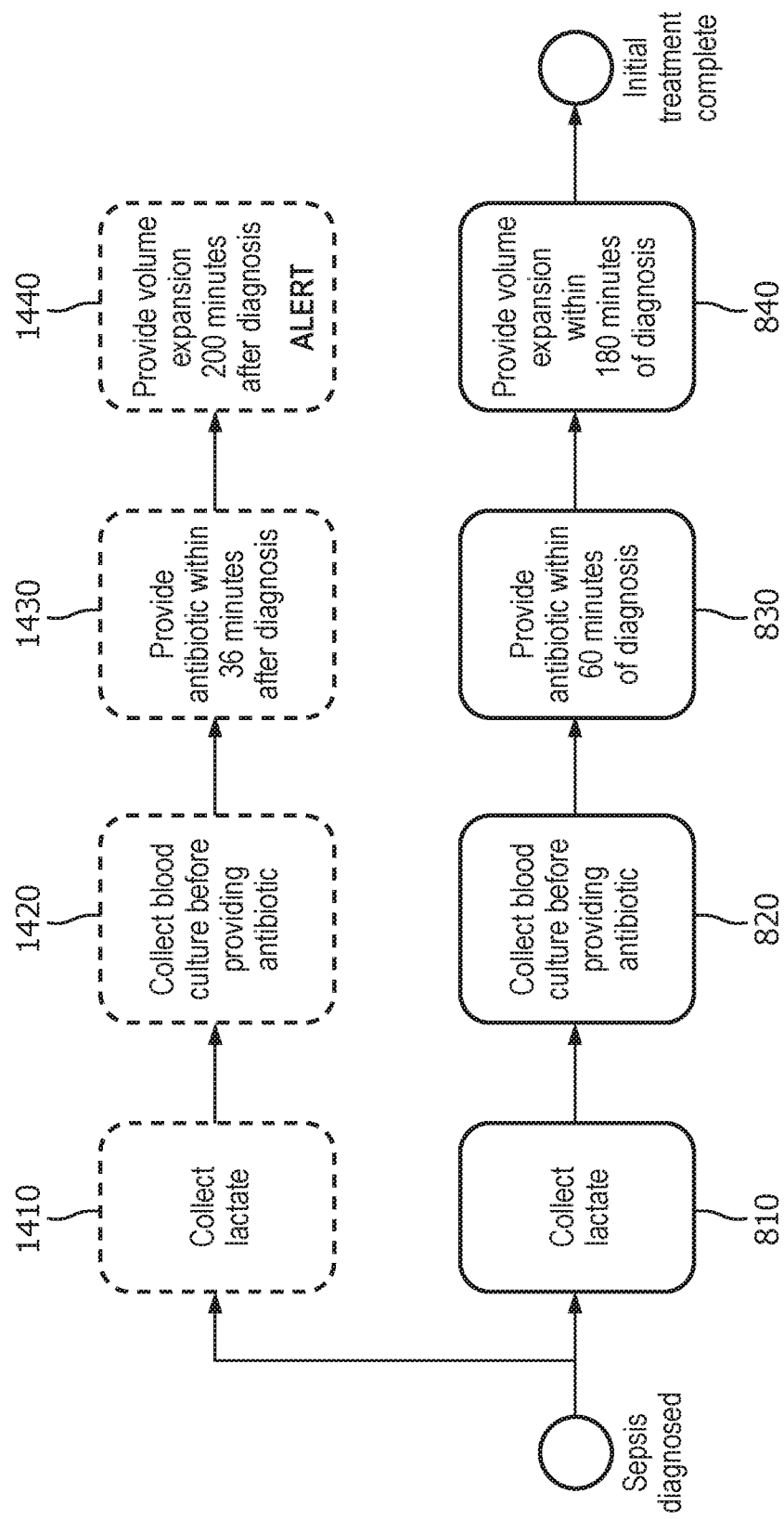
FIG. 14 is a graphical representation of an executable clinical pathway workflow comprising interventions/tasks, in accordance with an embodiment.

Referring to FIG. 14, in one embodiment, is a workflow graphical representation made by the system showing both the expected clinical pathway workflow with interventions 810 through 840, as well as the EMR information about the patient's actual treatment and status at 1410 through 1440. The rules executor or rules executor instructions 265 may, for example, compare the interventions 810 through 840 in the clinical pathway workflow with the EMR information about the patient's implemented treatment and status at 1410 through 1440. Comparing by the rules executor will comprise comparing the deviation rules for 810 with the report 1410, comparing the deviation rules for 820 with the report 1420, and so on.

In FIG. 14, the comparison of the deviation rules for 830 with the report 1430 fails to identify a deviation. There is a deviation rule for 830 that the antibiotic must be implemented within 60 minutes of the patient's diagnosis. Since the antibiotic was provided to the patient 36 minutes after diagnosis as shown in EMR information or report 1430, there is no deviation.

There is one or more deviation rules for 840 that there must be a volume expansion within 180 minutes after diagnosis. As shown in the EMR information or report 1430, the volume expansion was 200 minutes after diagnosis. This violates the deviation rule that there must be a volume expansion within 180 minutes after diagnosis. Accordingly, the rules executor identifies this late application of the second antibiotic as being a deviation.

According to one embodiment, it may be essential that the information from the EMR contains a timestamp and the role and/or identity of the individual implementing an intervention, in order to be able to apply the deviation rules. For example, a deviation rule regarding a specific healthcare position or role for implementation of an intervention cannot be utilized if the identity of the person implementing that intervention is not provided to the EMR or is not provided to the system by the EMR. Accordingly, the system may be configured to discard or ignore information about an intervention or patient if the information is: missing a timestamp or comprises an invalid timestamp, missing an identification or comprises an invalid identification, missing or comprising an invalid intervention identification, and so on. Thus, an embodiment of step 114 of the method comprises: (i) reviewing the information received from the EMR system for a timestamp, a personnel identification, or other necessary information; and (ii) discarding some or all of the information from the EMR system if that information is missing a timestamp, a personnel identification, and/or any other necessary information.

At step 116 of the method, according to an embodiment, the system alerts a user of the clinical pathways management system to the identified one or more deviations in the treatment action. According to an embodiment, the clinical pathways management system 200 alerts the user via a user interface 240 of the system, and/or via other mechanisms. The system may alert the user via any mechanism for alert, including but not limited to a visual display, an audible notification, a text message, an email, a page, or any other method of notification.

According to an embodiment, the alert includes displaying the identified deviation in a modified version of the graphical representation of the executable specific disease workflow. FIG. 8 is just one possible embodiment of such a display. According to an embodiment, the alert includes an identification of where in the implemented clinical workflow the deviation occurred.

At optional step 118 of the method, the identified deviation and possibly other information is stored within a local and/or remote log file by the system. For example, the information may be stored in storage 260 of the system, and/or in the EMR system 270. The system may save information about parameters of the clinical workflow and/or deviation such as the expected and actual actor, the expected and actual intervention, the expected and actual dosage, timing, and other factors.

At step 120 of the method, a healthcare professional user of the clinical pathways management system modifies and/or rectifies, in response to the alert, the treatment of the patient. Accordingly, the alert generated by the system is utilized by the healthcare professional as a treatment device for the patient. For example, the alert derived from the deviation identified in FIG. 8 may comprise information about the expected and actual actor, the expected and actual intervention, the expected and actual dosage, the expected and actual timing of the intervention, the identified deviation, the deviation rule violated, and/or other information. The healthcare professional receives this information and analyzes it to evaluate the effect(s) of the deviation, and to determine a course of action that obviates, rectifies, or otherwise addresses the deviation. The professional may or may not consult the clinical pathways management system for treatment suggestions.

Referring to the example in FIG. 15, which builds on FIG. 14, the healthcare professional receives an alert at 1440 indicating that volume expansion was 200 minutes after diagnosis which violates the deviation rule that there must be a volume expansion within 180 minutes after diagnosis. The late volume expansion may indicate, for example, that it will not be maximally effective and therefore a rectifying action is necessary to return the deviating clinical pathway to the expected clinical pathway. Accordingly, the healthcare professional orders a rectifying action. In FIG. 15, the rectifying action 1510 is to provide a volume expansion as soon as possible. This results in the deviating clinical pathway to return to the expected clinical pathway with an Initial Treatment Complete.

Referring to FIG. 2, in one embodiment, is a schematic representation of a clinical pathways management system 200. System 200 may be any of the systems described or otherwise envisioned herein, and may comprise any of the components described or otherwise envisioned herein. According to an embodiment, system 200 comprises one or more of a processor 220, memory 230, user interface 240, communications interface 250, and storage 260, interconnected via one or more system buses 212. It will be understood that FIG. 2 constitutes, in some respects, an abstraction and that the actual organization of the components of the system 200 may be different and more complex than illustrated.

According to an embodiment, system 200 comprises a processor 220 capable of executing instructions stored in memory 230 or storage 260 or otherwise processing data to, for example, perform one or more steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While clinical pathways management system 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an embodiment, storage 260 of clinical pathways management system 200 may store one or more algorithms, modules, and/or instructions to carry out one or more functions or steps of the methods described or otherwise envisioned herein. For example, processor 220 may comprise, among other instructions, reference ontology instructions 262, domain ontology instructions 263, rules generator instructions 264, rules executor instructions 265, and/or alerting instructions 266.

According to an embodiment, reference ontology instructions 262 direct the system to obtain and/or generate a reference ontology 310 comprising information about execution of a plurality of clinical pathways. The reference ontology provides a conceptual representation for a typical clinical pathway, which is usually a process consisting of multiple care phases. Each phase is associated with information such as a set of temporal constraints, which can include start time, expire time, and duration. According to an embodiment, the reference ontology comprises different classes and/or other methods of organization of properties and relations between data.

According to an embodiment, domain ontology instructions 263 direct the system to generate and/or define a domain ontology 320 for one or more of the clinical pathways utilized or monitored by the clinical pathways management system. According to an embodiment, defining a domain ontology comprises adding one or more subclasses about a specific disease or condition to one or more classes of the relevant reference ontology. One or more of the subclass may comprise information about one or more deviation boundaries.

According to an embodiment, rules generator instructions 264 direct the system to generate one or more workflow deviation rules using the defined domain ontology. As described herein, the rules generator utilizes the one or more constraints associated with an intervention or task to generate workflow deviation rules. For example, an intervention may comprise temporal constraints, sequential constraints, volumetric constraints, and/or professional role constraints, among many other types of constraints. The deviation rules created by the rules generator may use these constraints to define the boundaries or thresholds for the rules.

According to an embodiment, rules executor instructions 265 direct the system to compare received EMR information to the generated rules in order to identify whether a rule or constraint has been violated or exceeded. According to an embodiment, the identified deviation includes information about the deviation type and/or other information including but not limited to deviation type, workflow task/intervention, professional role, work shift and date/time of intervention, and/or any other information. The system receives data from EMR related to the care actions for that patient, which are flagged into the clinical pathway workflow. The rules executor instructions can direct the system to show the patient's status in the workflow graphical representation and can detect if any deviations have occurred in the clinical pathway, among other options.

According to an embodiment, alerting instructions 266 direct the system to alert a user of the clinical pathways management system to the identified one or more deviations in the treatment action. According to an embodiment, the clinical pathways management system 200 alerts the user via a user interface 240 of the system, and/or via other mechanisms. The system may alert the user via any mechanism for alert, including but not limited to a visual display, an audible notification, a text message, an email, a page, or any other method of notification.

According to an embodiment, system 200 is configured to receive, from a healthcare professional in response to the received alert and the identified one or more deviations from the first clinical pathway, one or more interventions for the patient. The healthcare professional receives information about a deviation as described herein and analyzes it to evaluate the effect(s) of the deviation, and to determine a course of action that obviates, rectifies, or otherwise addresses the deviation. The professional may or may not consult the clinical pathways management system for treatment suggestions. Accordingly, the alert generated by the system is utilized by the healthcare professional as a treatment device for the patient.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A tangible non-transitory computer readable medium that stores instructions for alerting a user of a clinical pathways management system to a clinical pathway deviation, wherein the instructions, when executed by a processor, cause the processor to:
   provide a reference ontology comprising information about implementation of a plurality of clinical pathways, the reference ontology comprising a plurality of classes;
   define a domain ontology by adding one or more subclasses to each of the plurality of classes of the reference ontology, wherein each added subclass comprises one or more deviation boundaries;
   convert the domain ontology to one or more graphical representations of clinical pathways, wherein each clinical pathway comprises one or more interventions;
   generate one or more deviation rules for a plurality of the clinical pathways, including a first clinical pathway, based on the one or more deviation boundaries, the one or more deviation rules being encoded in a semantic web language format;
   translate the one or more deviation rules from the semantic web language format to logic statements, and populate a relational database table with the translated one or more deviation rules, wherein the logic statements comprise if-then-if statements stored in the relational database table;
   receive information about one or more interventions relative to a patient being treated using the first clinical pathway;
   access the relational database table for comparing the received information about one or more interventions with the translated one or more deviation rules for the first clinical pathway in order to identify one or more deviations from the first clinical pathway; and
   provide an alert, via a user interface, to the user of the clinical pathways management system for the identified one or more deviations from the first clinical pathway, wherein the alert comprises a display of the identified one or more deviations from the first clinical pathway in the one or more graphical representations of the first clinical pathway.

2. The tangible non-transitory computer readable medium of claim 1, wherein the instructions further cause the processor to modify, in response to the alert and the identified one or more deviations from the first clinical pathway, one or more interventions for the patient.

3. The tangible non-transitory computer readable medium of claim 1, wherein the instructions further cause the processor to discard the received information about one or more interventions relative to a patient being treated using a first clinical pathway, if the received information is missing a timestamp or personnel identification.

4. The tangible non-transitory computer readable medium of claim 1, wherein the alert comprises an identification of where in the first clinical pathway the identified one or more deviations occurred.

5. The tangible non-transitory computer readable medium of claim 1, wherein the reference ontology is based at least in part on a plurality of clinical reports relevant to a plurality of clinical pathways.

6. The tangible non-transitory computer readable medium of claim 1, wherein the deviation rules comprise temporal constraints, sequential constraints, volumetric constraints, and/or professional role constraints.

7. The tangible non-transitory computer readable medium of claim 1, wherein the domain ontology is converted to one or more graphical representations of clinical pathways using Business Process Model and Notation (BPMN).

8. The tangible non-transitory computer readable medium of claim 1, wherein the semantic web language format comprises an ontology web language (OWL) format.

9. A system configured to alert a user to a clinical pathway deviation, the system comprising:
   a tangible, non-transitory computer readable medium that stores: a reference ontology comprising a plurality of classes of information about implementation of a plurality of clinical pathways; and a domain ontology, comprising one or more subclasses added to plurality of classes, wherein each subclass comprises one or more deviation boundaries; and instructions; and
   a processor that executes the instructions causing the processor to: (i) convert the domain ontology to one or more graphical representations of clinical pathways, wherein each clinical pathway comprises one or more interventions; (ii) generate, using the one or more deviation boundaries of the domain ontology, one or more deviation rules for a plurality of the clinical pathways, including a first clinical pathway, the one or more deviation rules being encoded in a semantic web language format; (iii) translate the one or more deviation rules to logic statements, and populate a relational database table with the translated one or more deviation rules, wherein the logic statements comprise if-then-if statements stored in the relational database table; (iv) receive information about one or more interventions relative to a patient being treated using the first clinical pathway; (v) access the relational database table for comparing the received information about one or more interventions with the translated one or more deviation rules for the first clinical pathway in order to identify one or more deviations from the first clinical pathway; and (vi) alert, via a user interface, the user of the system to the identified one or more deviations from the first clinical pathway, wherein the alert comprises a display of the identified one or more deviations from the first clinical pathway in the one or more graphical representations of the first clinical pathway.

10. The system of claim 9, wherein the domain ontology is converted to the one or more graphical representations of clinical pathways using a Business Process Model and Notation (BPMN).

11. The system of claim 9, wherein the deviation rules comprise temporal constraints, sequential constraints, volumetric constraints, and/or professional role constraints.

12. The system of claim 9, wherein the reference ontology is based at least in part on a plurality of clinical reports relevant to a plurality of clinical pathways.

13. The system of claim 9, wherein the alert comprises an identification of where in the first clinical pathway the identified one or more deviations occurred.

14. The system of claim 9, wherein the instructions further cause the processor to discard the received information about one or more interventions relative to a patient being treated using a first clinical pathway, if the received information is missing a timestamp or personnel identification.

15. The system of claim 9, wherein the alert comprises an identification of where in the first clinical pathway the identified one or more deviations occurred.

16. The system of claim 9, wherein the instructions further cause the processor to generate deviation rules using first order logic, translate the deviation rules into an if-then-else format, and store the if-then-else format in the relational database table.

* * * * *